US012611169B2

(12) United States Patent
Jenkins et al.

(10) Patent No.: US 12,611,169 B2
(45) Date of Patent: Apr. 28, 2026

(54) INTRALUMINAL ULTRASOUND IMAGING WITH AUTOMATIC AND ASSISTED LABELS AND BOOKMARKS

(71) Applicant: PHILIPS IMAGE GUIDED THERAPY CORPORATION, San Diego, CA (US)

(72) Inventors: Rebecca Ann Jenkins, San Diego, CA (US); Pei-Yin Chao, Eindhoven (NL); Nikhil Sreedhar Rajguru, San Diego, CA (US); Tracy LeFever, Andover, MA (US); Carl Rowe, Andover, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/433,156

(22) Filed: Feb. 5, 2024

(65) Prior Publication Data

US 2024/0206846 A1 Jun. 27, 2024

Related U.S. Application Data

(63) Continuation of application No. 16/663,494, filed on Oct. 25, 2019, now Pat. No. 11,890,137.

(Continued)

(51) Int. Cl.
A61B 8/12 (2006.01)
A61B 8/00 (2006.01)
(Continued)

(52) U.S. Cl.
CPC ................ *A61B 8/12* (2013.01); *A61B 8/463* (2013.01); *A61B 8/468* (2013.01); *A61B 8/5207* (2013.01);
(Continued)

(58) Field of Classification Search
CPC ........... A61B 8/12; A61B 8/463; G06F 3/167; G16H 30/40; G06T 11/60
See application file for complete search history.

(56) References Cited

U.S. PATENT DOCUMENTS 6,200,268 B1 3/2001 Vince
6,381,350 B1 4/2002 Klingensmith
(Continued)

FOREIGN PATENT DOCUMENTS

CN 107019513 A 8/2017
WO 2014055908 A2 4/2014
(Continued)

*Primary Examiner* — Nyrobi Celestine

(57) ABSTRACT

Disclosed is an intraluminal ultrasound imaging system, including a processor circuit in communication with an intraluminal ultrasound imaging catheter, and configured to receive a plurality of intraluminal ultrasound images from the imaging catheter during movement of the imaging catheter within a body lumen of a patient, the body lumen comprising a plurality of segments. The processor circuit is further configured to generate a marker to be applied to an intraluminal ultrasound image of the plurality of intraluminal ultrasound images, wherein the marker is generated based on the movement of the intraluminal ultrasound imaging catheter, and wherein the marker is representative of a segment of the plurality of segments, and output to a display the marker and the plurality of intraluminal ultrasound images shown successively.

16 Claims, 11 Drawing Sheets

Related U.S. Application Data

(60) Provisional application No. 62/751,268, filed on Oct. 26, 2018.

(51) Int. Cl.
| | |
|---|---|
| *G06F 3/0486* | (2013.01) |
| *G06F 3/0488* | (2022.01) |
| *G06F 3/16* | (2006.01) |

(52) U.S. Cl.
CPC .......... *A61B 8/5292* (2013.01); *G06F 3/0486* (2013.01); *G06F 3/0488* (2013.01); *G06F 3/167* (2013.01)

(56) References Cited

U.S. PATENT DOCUMENTS

| | | | |
|---|---|---|---|
| 7,074,188 B2 | 7/2006 | Nair | |
| 7,175,597 B2 | 2/2007 | Vince | |
| 7,215,802 B2 | 5/2007 | Klingensmith | |
| 7,359,554 B2 | 4/2008 | Klingensmith | |
| 7,463,759 B2 | 12/2008 | Klingensmith | |
| 7,846,101 B2 | 12/2010 | Eberle | |
| 10,376,165 B2 | 8/2019 | Lavi | |
| 2002/0087061 A1 | 7/2002 | Lifshitz | |
| 2002/0171669 A1 | 11/2002 | Meron | |
| 2006/0241465 A1* | 10/2006 | Huennekens | A61B 5/06 |
| | | | 600/458 |
| 2006/0241469 A1 | 10/2006 | Rold | |
| 2007/0268280 A1 | 11/2007 | Fujita | |
| 2008/0110261 A1 | 5/2008 | Randall | |
| 2008/0112604 A1 | 5/2008 | Lloyd | |
| 2011/0034801 A1 | 2/2011 | Baumgart | |

| | | | |
|---|---|---|---|
| 2012/0087562 A1 | 4/2012 | Isaacs | |
| 2013/0079630 A1 | 3/2013 | Horiike | |
| 2013/0267848 A1 | 10/2013 | Fearnot | |
| 2014/0094660 A1 | 4/2014 | Tolkowsky | |
| 2014/0100454 A1* | 4/2014 | Kemp | A61B 8/12 |
| | | | 600/407 |
| 2014/0187920 A1* | 7/2014 | Millett | A61B 6/504 |
| | | | 600/424 |
| 2014/0270436 A1 | 9/2014 | Dascal | |
| 2014/0282142 A1 | 9/2014 | Lin | |
| 2014/0324475 A1 | 10/2014 | Ochi | |
| 2015/0005630 A1 | 1/2015 | Jung | |
| 2015/0119705 A1 | 4/2015 | Tochterman | |
| 2015/0230775 A1 | 8/2015 | Kobayashi | |
| 2016/0015327 A1* | 1/2016 | Merritt | A61B 5/0215 |
| | | | 600/486 |
| 2016/0022208 A1 | 1/2016 | Gopinath | |
| 2016/0135787 A1* | 5/2016 | Anderson | A61B 8/12 |
| 2016/0157787 A1 | 6/2016 | Merritt | |
| 2016/0157808 A1 | 6/2016 | Merritt | |
| 2016/0206267 A1 | 7/2016 | Shimizu | |
| 2016/0335763 A1 | 11/2016 | Ambwani | |
| 2016/0335766 A1 | 11/2016 | Ambwani | |
| 2017/0032523 A1 | 2/2017 | Klaiman | |
| 2017/0103520 A1* | 4/2017 | Gopinath | G06T 19/00 |
| 2019/0282199 A1 | 9/2019 | Merritt | |
| 2019/0282211 A1* | 9/2019 | Merritt | |
| 2020/0029932 A1* | 1/2020 | Cohen | A61B 8/5223 |

FOREIGN PATENT DOCUMENTS

| | | | | |
|---|---|---|---|---|
| WO | WO-2016187218 A1 * | 11/2016 | | G06T 7/70 |
| WO | 2017066108 A1 | 4/2017 | | |
| WO | 2019175004 A1 | 9/2019 | | |

* cited by examiner

INTRALUMINAL ULTRASOUND IMAGING WITH AUTOMATIC AND ASSISTED LABELS AND BOOKMARKS

CROSS REFERENCE TO RELATED APPLICATIONS

This application is U.S. patent application Ser. No. 16/663,494, filed Oct. 25, 2019, now U.S. Pat. No. 11,890, 137, which claims priority to and the benefit of U.S. Provisional Patent Application No. 62/751,268, filed Oct. 26, 2018, each of which is incorporated by reference herein in its entirety.

TECHNICAL FIELD

The subject matter described herein relates to a system for medical imaging. In particular, the disclosed system provides a system for bookmarking and labeling peripheral intravascular ultrasound or IVUS images during a pullback procedure. This system has particular but not exclusive utility for diagnosis and treatment of vascular diseases.

BACKGROUND

Peripheral vascular procedures, such as angioplasty and stenting in peripheral venous (Inferior Vena Cava—IVC, iliac, femoral veins), IVC-filter retrieval, EVAR and FEVAR (and similar on the abdominal trait) atherectomy and thrombectomy are procedures where IVUS is used. Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. A stent is a dense (e.g., metallic) object that may be placed in a vessel or lumen to hold the vessel or lumen open to a particular diameter. A compression occurs when anatomical structures outside the vessel or lumen impinge on the vessel or lumen, constricting it.

In some cases, intraluminal medical imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

Labelling and annotations are often repetitive and time consuming in a typical IVUS workflow. Additionally, while placing bookmarks, the time between the physician or other user calling for bookmarks and actual placement of bookmark can lead to placement of the bookmark on a frame not originally intended by the physician or other user. In these cases, the physician or other user often has to go back and find the right frame of interest for further investigation, measurement, or analysis. Current methods of bookmarking/ labelling often include selection from a pick list or editing that involves manual interaction by a user. Often, the saved bookmark includes only generic text that must later be customized or elaborated by the clinician.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for advantageously tagging, labeling, and annotating intraluminal images from an intraluminal medical imaging sequence (e.g., an IVUS pullback sequence) using labels automatically (e.g., predictively) provided by the system, or else selected by a user from a short list automatically provided by the system, thus permitting rapid, accurate real-time bookmarking of the location and severity of diseases or compressions of the lumen, along with reference images, post-treatment images, and other images. The system is hereinafter referred to as an automatic and assisted bookmarking system.

Automatically generated or assistive-ly suggested labels/ bookmarks for IVUS make the placement of labels/bookmarks simpler and faster than is currently possible. By having the user select a procedure type such as coronary/ peripheral, venous or arterial, the system is able to supply a list of relevant bookmarks for the user to select. The user can drag and drop the labels/bookmarks where appropriate, and can also edit labels and bookmarks as needed. Labels and bookmarks can be automated, semi-automated or user driven. Bookmarks can also provide a selectable range of neighboring frames to choose from.

The automatic and assisted bookmarking system disclosed herein has particular, but not exclusive, utility for intraluminal ultrasound imaging procedures. One general aspect includes an intraluminal ultrasound imaging system, including: a processor circuit configured for communication with an intraluminal ultrasound imaging catheter, where the processor circuit is configured to: receive a plurality of intraluminal ultrasound images obtained by the intraluminal ultrasound imaging catheter during movement of the intraluminal ultrasound imaging catheter within a body lumen of a patient, the body lumen including a plurality of segments; generate a marker to be applied to an intraluminal ultrasound image of the plurality of intraluminal ultrasound images, where the marker is generated based on the movement of the intraluminal ultrasound imaging catheter, and where the marker is predictive and/or representative of a segment of the plurality of segments; and output, to a display in communication with the processor circuit, a screen display including the marker and the plurality of intraluminal ultrasound images. Other embodiments of this aspect include corresponding computer systems, apparatus, and computer programs recorded on one or more computer storage devices, each configured to perform the actions of the methods.

Implementations may include one or more of the following features. The system further including a user interface, where the processor circuit is configured to receive a user input, via the user interface, to apply the marker to the intraluminal ultrasound image of the plurality of intraluminal ultrasound images. The system where, in response to the receiving the user input to apply the marker, the processor circuit is configured to apply with the marker one or more other intraluminal ultrasound images neighboring the intraluminal ultrasound image. The system where the display includes a touchscreen, and where the user interface includes a drag-and-drop interface on the touchscreen, and where the user input includes a drag-and-drop input. The system where the user interface includes a voice recognition interface, and the user input includes a spoken confirmation. The system where the processor circuit is further configured to output stylized diagram of the body lumen including the plurality of segments, where the marker identifies a location in the stylized diagram where the segment begins. The system where the processor circuit is configured to: generate a plurality of markers to be applied to the plurality of ultrasound images; and output the plurality of markers successively, where each of the plurality of markers corresponds to a different segment of the plurality of segments. The system where the processor circuit is configured to determine an order for the successive output of the plurality of markers based on the movement of the intraluminal ultrasound imaging catheter. The system where the processor circuit is configured to determine the order based on at least one of an access point to the body lumen or a direction of movement of the intraluminal ultrasound imaging catheter. The system further including the intraluminal ultrasound imaging catheter, where the intraluminal ultrasound imaging catheter includes an intravascular ultrasound (IVUS) imaging catheter, and where the body lumen includes a peripheral blood vessel. Implementations of the described techniques may include hardware, a method or process, or computer software on a computer-accessible medium.

One general aspect includes an intraluminal ultrasound imaging system, including: a processor circuit configured for communication with an intraluminal ultrasound imaging catheter, where the processor circuit is configured to: receive an intraluminal ultrasound image obtained by the intraluminal ultrasound imaging catheter during movement of the intraluminal ultrasound imaging catheter within a body lumen of a patient; generate a plurality of text labels; output a screen display including a first portion includes the intraluminal ultrasound image and a second portion including the plurality of text labels, where the first portion is proximate to the second portion; receive a drag-and-drop user input moving a text label of the plurality of text labels from the second portion to the first portion; and associate the text label with the intraluminal ultrasound image. Other embodiments of this aspect include corresponding computer systems, apparatus, and computer programs recorded on one or more computer storage devices, each configured to perform the actions of the methods.

One general aspect includes an intraluminal ultrasound imaging method, including: receiving, at a processor circuit in communication with an intraluminal ultrasound imaging catheter, a plurality intraluminal ultrasound images obtained by the intraluminal ultrasound imaging catheter during movement of the intraluminal ultrasound imaging catheter within a body lumen of a patient, the body lumen including a plurality of segments; generating a marker to be applied to an intraluminal ultrasound image of the plurality intraluminal ultrasound images, where the marker is generated based on the movement of the intraluminal ultrasound imaging catheter, and where the marker is predictive and/or representative of a segment of the plurality of segments; and outputting, to a display in communication with the processor circuit, a screen display including the marker and the plurality of intraluminal ultrasound images shown successively. Other embodiments of this aspect include corresponding computer systems, apparatus, and computer programs recorded on one or more computer storage devices, each configured to perform the actions of the methods.

Implementations may include one or more of the following features. The method further including receiving a user input, via a user interface operating on the processor circuit, to apply the marker to the intraluminal ultrasound image of the plurality of intraluminal ultrasound images. The method further including, in response to the receiving the user input to apply the marker, applying the marker to one or more other intraluminal ultrasound images neighboring the intraluminal ultrasound image. The method where the display includes a touchscreen, and where the user interface includes a drag-and-drop interface on the touchscreen, and where the user input includes a drag-and-drop input. The method where the user interface includes a voice recognition interface, and the user input includes a spoken confirmation. The method further including outputting a stylized diagram of the body lumen including the plurality of segments, where the marker identifies a location in the stylized diagram where the segment begins. The method further including: generating a plurality of markers to be applied to the plurality of ultrasound images; and outputting, to the display in communication with the processor circuit, a screen display including the plurality of markers successively, where each of the plurality of markers corresponds to a different segment of the plurality of segments. The method further including determining an order for the successive output of the plurality of markers based on the movement of the intraluminal ultrasound imaging catheter. The method further including determining the order based on at least one of an access point to the body lumen or a direction of movement of the intraluminal ultrasound imaging catheter. Implementations of the described techniques may include hardware, a method or process, or computer software on a computer-accessible medium.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the automatic and assisted bookmarking system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
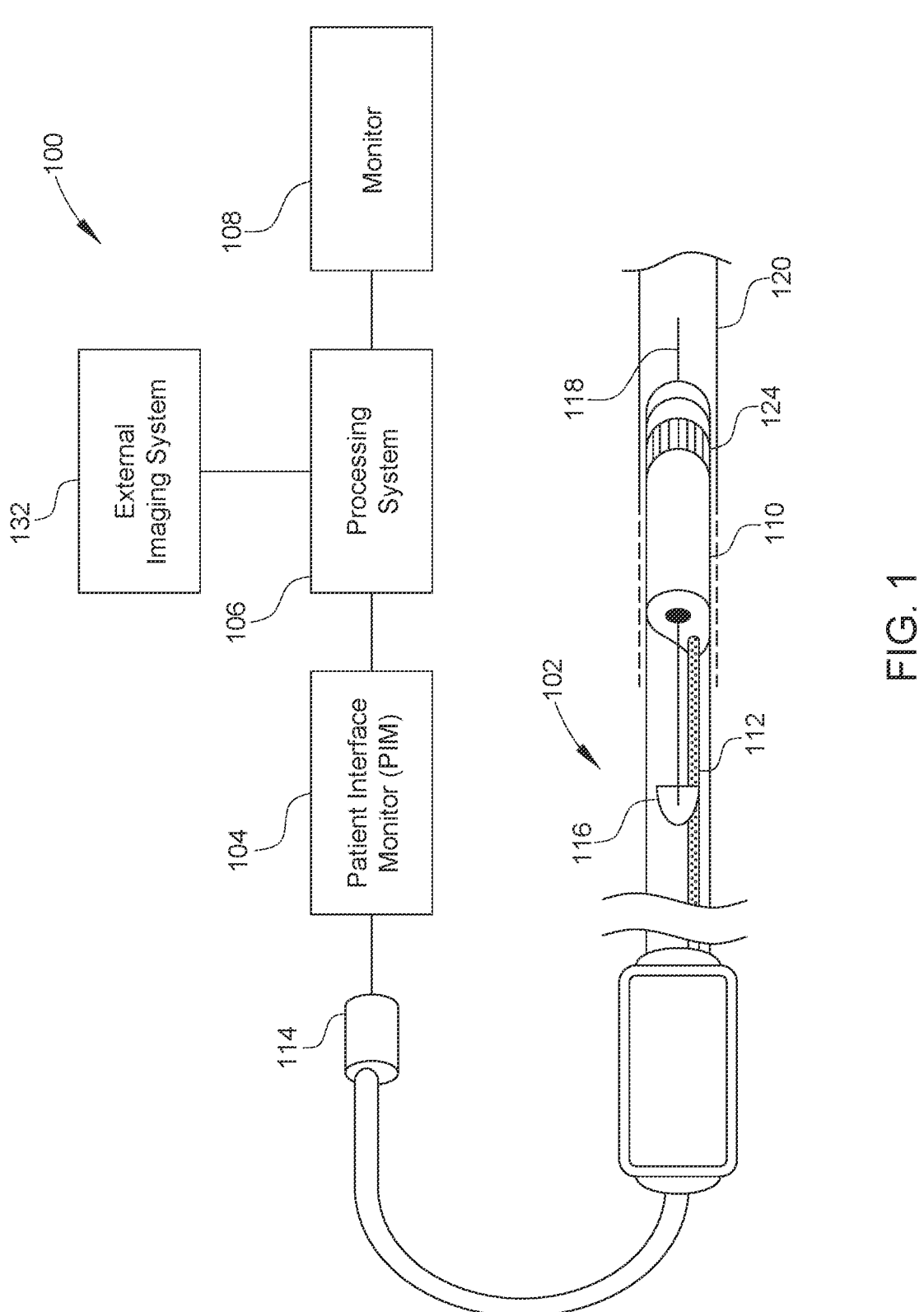
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes systems, devices, and methods for labeling and bookmarking intraluminal images during an intraluminal imaging procedure such as an IVUS pullback. Drag and drop labels and bookmarks are provided to users to enable a simpler and faster way of placing labels and bookmarks. Appropriate labels and bookmarks appear based on user selections including procedure type (coronary/peripheral, venous/arterial, etc.), entry point, entry direction or pullback direction, and disease type. Labels and bookmarks contain information such as anatomical references or disease states/types. Using confirmation inputs from the user, the system is able to place the labels and bookmarkers where and when appropriate. The system also makes it possible to customize or edit labels and bookmarks. Labels and bookmarks can be saved to the IVUS image, ILD, graphical representation of anatomy, pre/post images, roadmap images, and reports. On the anatomical map, automated labels would appear in successive order to allow users to correctly label anatomical segments, as well as segments or sub-segments within the segments (e.g., a lesion/plaque buildup, an area of compression, healthy tissue used as a reference, etc.). The creation of labels or bookmarks can be automated, semi-automated or user driven, according to aspects of the present disclosure.

The automatic and/or assisted bookmarking system provides easy and fast placement of labels and bookmarks using (for example) drag and drop functionality, not only to the IVUS image itself but to an ILD, graphical roadmap or other graphical representation of anatomy, for both pre- and post-treatment images. In an example, the processor circuit is receiving an electrical signal representative of the drag and drop input. Depending on the application, a list of commonly used labels for anatomical locations/disease states is created for coronary/peripheral and venous/arterial procedures, and accessed by the user via drag and drop functionality. Additionally, a user of the system is able to manually edit labels and/or bookmarks as desired, if necessary. This system is hereinafter referred to as an automatic and assisted bookmarking system.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. 62/642,847, filed Mar. 14, 2018 (and a Non-Provisional Application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional Application filed therefrom on Mar. 15, 2019 as U.S. Ser. No. 16/354,970), each of which is hereby incorporated by reference in its entirety as though fully set forth herein.

The present disclosure substantially aids a clinician in making sense of large volumes of intraluminal imaging data, along with reporting and treatment planning, plus reduced case time and improved ease of use. The present disclosure accomplishes this by providing a quick, seamless process for identification, marking, and annotation of locations of interest within a vessel or lumen along an examined length, in real time during the imaging procedure (e.g., an IVUS pullback procedure). Implemented on a medical imaging console (e.g., an IVUS imaging console) in communication with a medical imaging sensor (e.g., an intraluminal ultrasound sensor), the automatic and assisted bookmarking system disclosed herein provides both time savings and an improvement in the accuracy of bookmarking and labeling of captured images. This improved imaging workflow transforms a time-consuming process of imaging, image selection, data entry, review, and revision into a streamlined process involving both fewer steps and simpler steps. This occurs for example without the normally routine need for secondary or non-sterile users to type in bookmark and label data in real time, along with the associated time lags. This unconventional approach improves the functioning of the medical imaging console and sensor, by automating bookmarking and labeling steps that are normally performed manually by the clinician or other users.

The automatic and assisted bookmarking system may be implemented as a set of logical branches and mathematical operations, whose outputs are viewable on a display, and operated by a control process executing on a processor that accepts user inputs (e.g., from a user interface such as a keyboard, mouse, or touchscreen interface), and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment).

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

In some embodiments, the automatic and assisted bookmarking system includes screen displays that provide a clinician with a suggested "next bookmark" representing an upcoming region of interest, along with associated label information, that the clinician or another user can simply confirm when the desired intraluminal imaging frame from within the region of interest appears on the display.

When recording an IVUS pullback, the IVUS system successively stacks a cross-section of each recorded tomographic frame onscreen. The resulting image stack is called the In Line Digital or Image Longitudinal Display (ILD) view. Bookmarks can be automatically associated with the intraluminal image itself, as well as the ILD and/or a roadmap or graphical roadmap image, and reports generated therefrom.

IVUS pullback measurements results require recording, bookmarking, labeling, annotation, and reporting on the part of the clinician. The automatic and assisted bookmarking system eases the workload on the clinician, and permits certain aspects of bookmarking, labeling annotation and reporting to happen automatically during the IVUS procedure itself.

These descriptions are provided for exemplary purposes only, and should not be considered to limit the scope of the automatic and assisted bookmarking system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the automatic and assisted bookmarking system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System (HIS) via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user as any of the displays or visualizations shown in FIGS. 5-11.

The external imaging system 132 can be configured to obtain x-ray, radiographic, angiographic/venographic (e.g., with contrast), and/or fluoroscopic (e.g., without contrast) images of the body of a patient (including the vessel 120). External imaging system 132 may also be configured to obtain computed tomography images of the body of the patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
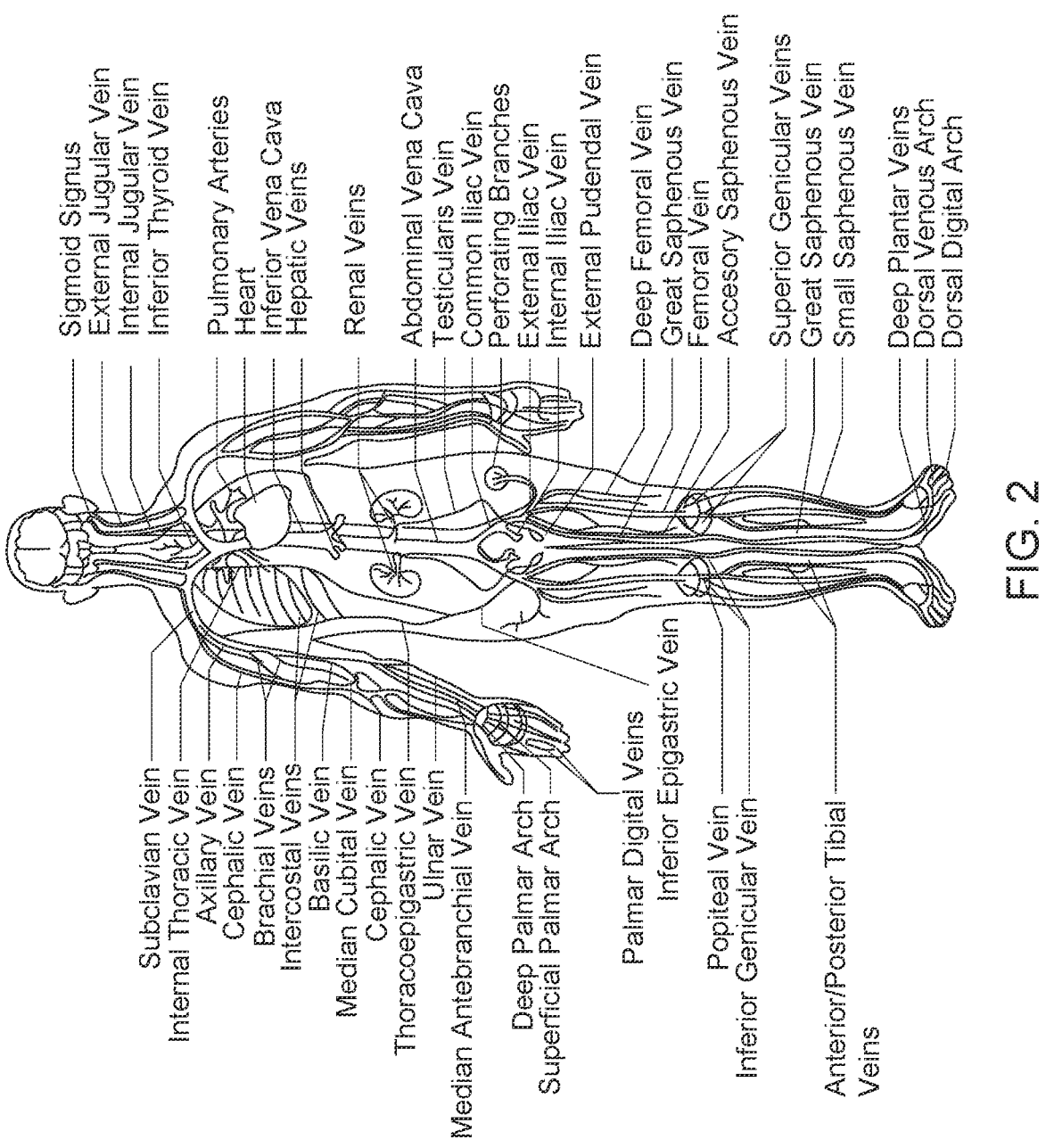
FIG. 2 illustrates blood vessels (e.g., arteries and veins) in the human body.

FIG. 2 illustrates blood vessels (e.g., arteries and veins) in the human body. For example, veins of the human body are labeled. Aspects of the present disclosure can be related to peripheral vasculature, e.g., veins in the torso or legs.

Occlusions can occur in arteries or veins. An occlusion can be generally representative of any blockage or other structural arrangement that results in a restriction to the flow of fluid through the lumen (e.g., an artery or a vein), for example, in a manner that is deleterious to the health of the patient. For example, the occlusion narrows the lumen such that the cross-sectional area of the lumen and/or the available space for fluid to flow through the lumen is decreased. Where the anatomy is a blood vessel, the occlusion may be a result of narrowing due to compression (e.g. from external vessels), plaque buildup, including without limitation plaque components such as fibrous, fibro-lipidic (fibro fatty), necrotic core, calcified (dense calcium), blood, and/or different stages of thrombus (e.g., acute, sub-acute, chronic, etc.). In some instances, the occlusion can be referenced as thrombus, a stenosis, and/or a lesion. Generally, the composition of the occlusion will depend on the type of anatomy being evaluated. Healthier portions of the anatomy may have a uniform or symmetrical profile (e.g., a cylindrical profile with a circular cross-sectional profile). The occlusion may not have a uniform or symmetrical profile. Accordingly, diseased or compressed portions of the anatomy, with the occlusion, will have a non-symmetric and/or otherwise irregular profile. The anatomy can have one occlusion or multiple occlusions.

Build-up of occlusion (e.g., thrombus, deep vein thrombosis or DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow therethrough. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

Figure 3:
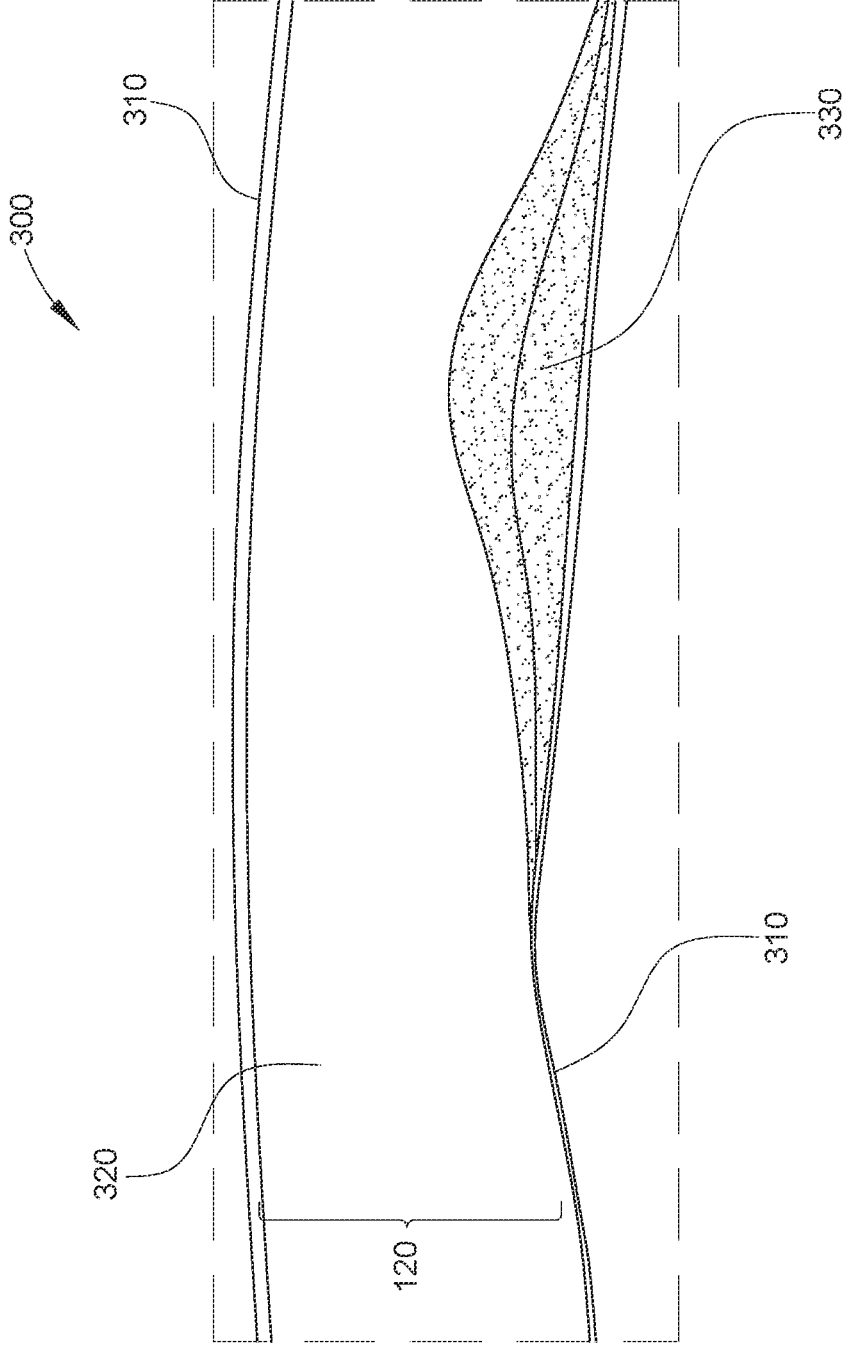
FIG. 3 illustrates a blood vessel incorporating a compression.

FIG. 3 illustrates a blood vessel 300 incorporating a compression 330. The compression 330 occurs outside the vessel walls 310 and may restrict the flow of blood 320. The compression may be caused by other anatomical structures outside the blood vessel 300, including but not limited to a tendon, ligament, or neighboring lumen.

Figure 4:
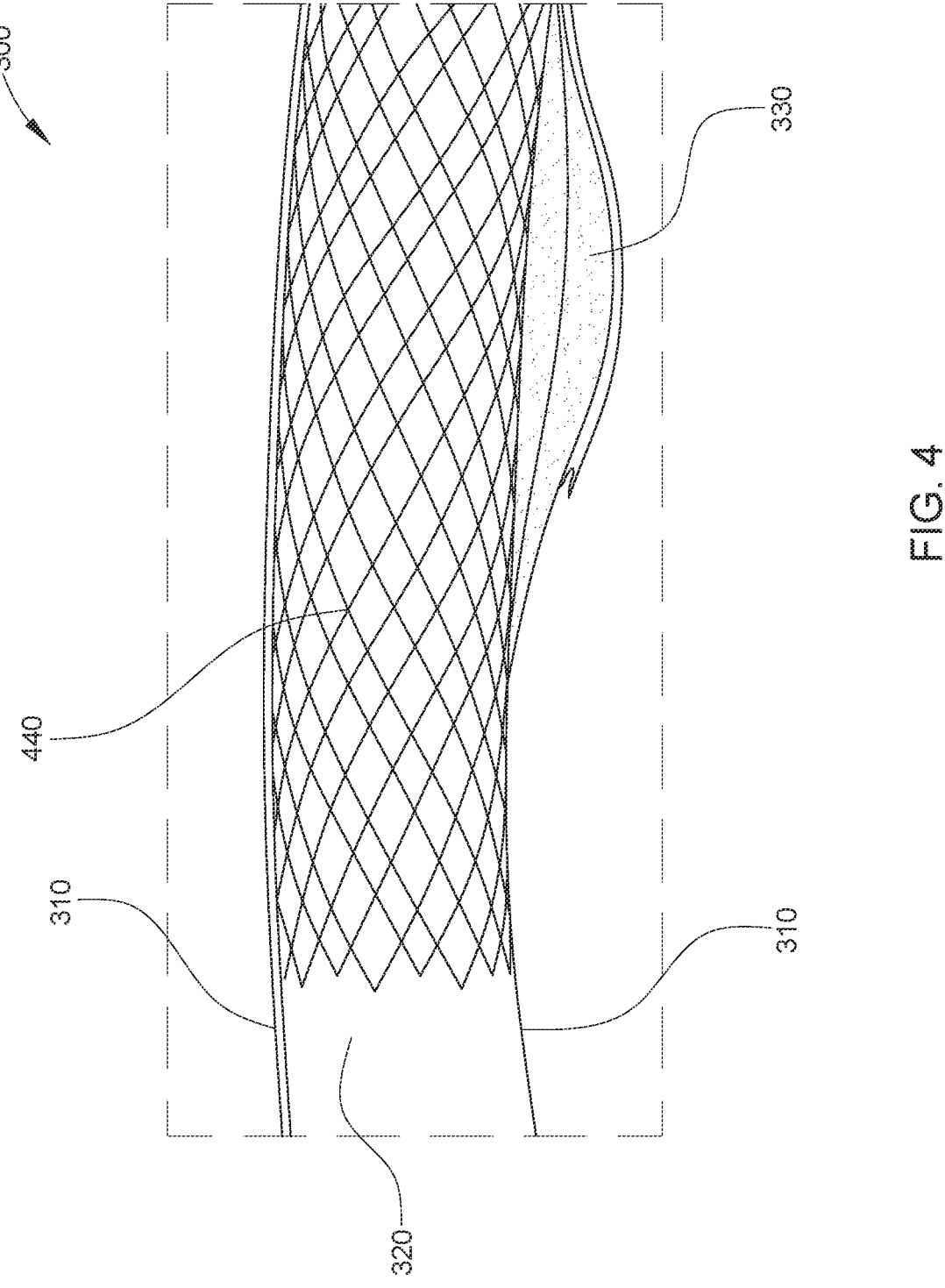
FIG. 4 illustrates a blood vessel incorporating a compression and with a stent expanded inside it to restore flow.

FIG. 4 illustrates a blood vessel 300 incorporating a compression 330 and with a stent 440 expanded inside it to restore flow. The stent 440 displaces and arrests the compression 330, pushing the vessel walls 310 outward, thus reducing the flow restriction for the blood 320. Other treatment options for alleviating an occlusion may include but are not limited to thrombectomy, ablation, angioplasty, and pharmaceuticals. However, in a large majority of cases it may be highly desirable to obtain accurate and timely intravascular images of the affected area, along with accurate and detailed knowledge of the location, orientation, length, and volume of the affected area prior to, during, or after treatment.

Figure 5:
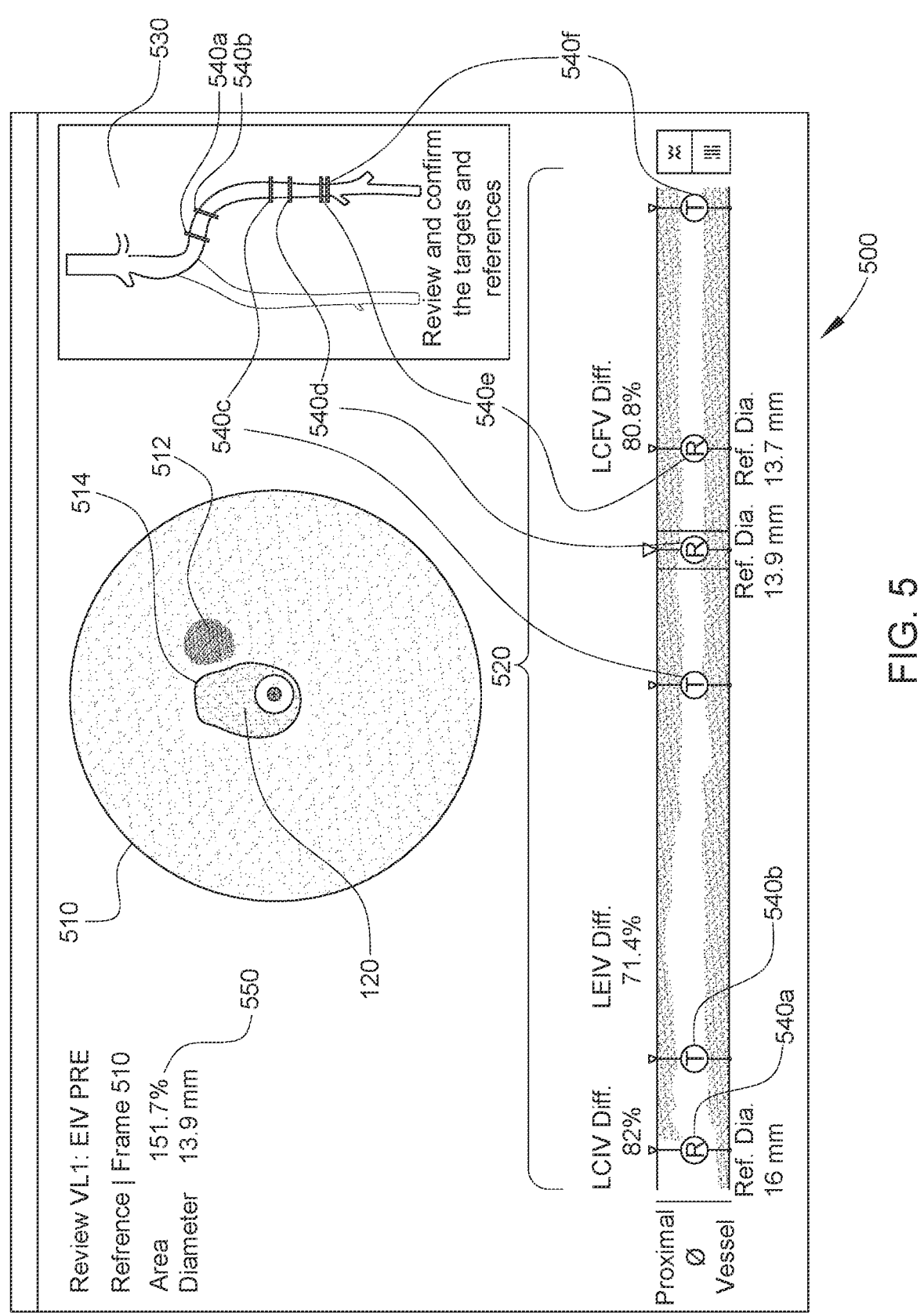
FIG. 5 illustrates an example intraluminal imaging display screen in accordance with at least one embodiment of the present disclosure.

FIG. 5 illustrates an example intraluminal imaging display screen 500 in accordance with at least one embodiment of the present disclosure. In this example, the screen display 500 includes a current tomographic IVUS image 510 from a series of successive tomographic images, an Image Longitudinal Display (ILD) 520 containing stacked longitudinal cross-sections of the series of successive tomographic images, and a graphical roadmap 530. Also visible are bookmarks 540a, 540b, 540c, 540d, 540e, and 540f, that are associated with both the graphical roadmap 530 and the ILD 520. Bookmark 540d is also associated with the current IVUS image 510, as is a label 550 that contains information about the location and nature of the IVUS image 510. In this example, the IVUS image is identified as a reference image of the left external iliac vein. In addition, the bookmark information can be saved to reports that are automatically generated. If a change to the bookmark is made in any of these locations, the automatic and assisted bookmarking system updates the bookmark in all of these locations, thus saving time and simplifying the bookmark editing workflow.

Figure 6:
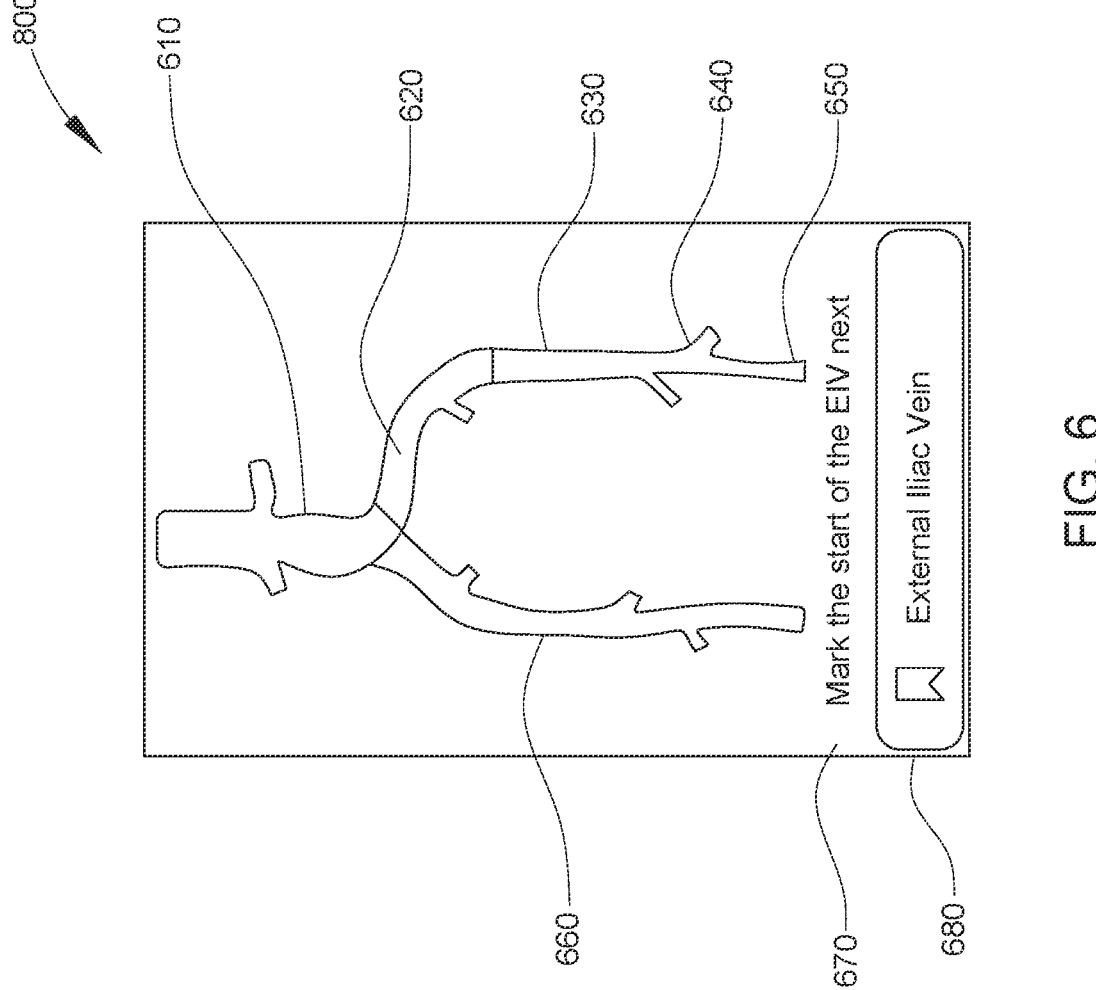
FIG. 6 shows a graphical roadmap screen display of an exemplary automatic and assisted bookmarking system during a pullback procedure in a left leg vein of a patient, in accordance with at least one embodiment of the present disclosure.

FIG. 6 shows a graphical roadmap screen display 530 of an exemplary automatic and assisted bookmarking system during a pullback procedure in a left leg vein of a patient, in accordance with at least one embodiment of the present disclosure. In this example, the graphical roadmap screen display includes multiple vein segments: the inferior vena cava (IVC) 610, the left common iliac vein (CIV) 620, the left external iliac vein (EIV) 630, left common femoral vein (CFV) 640, and a left femoral vein (F) 650. The corresponding segments on the right side 660 are also shown for reference, but are grayed out to indicate they are not part of the current procedure and will not be traversed by the intraluminal imaging probe during the procedure. Other vessel segments or lumen segments may be identified in other areas of the body. In some embodiments, the identification of vessel segments is performed automatically by the automatic and assisted bookmarking system (e.g., using image recognition, speed tracking, and position estimation), and bookmarks are automatically applied. In other embodiments, bookmarks are predictively suggested to the clinician or other user. Predicting the next bookmark that the user will need advantageously avoids a requirement for the user to look through a list of bookmarks to find the correct one, or type in a manual bookmark. In other embodiments, the identification of vessel segments is performed by a clinician or other user with the assistance of the automatic and assisted bookmarking system. Bookmarks or labels can be applied for example to a location where the segment begins or ends, or another segment begins or ends.

In the example shown in FIG. 6, the automatic and assisted bookmarking system is offering the clinician or other user an instruction 670 and a bookmark 680 that are based on the system's knowledge of the procedure being performed, the current location and movement direction of the intraluminal imaging probe 102 within the lumen 300, the proximity of anatomical landmarks (e.g., branches of the lumen or of neighboring lumens), and other information as necessary to perform the function. When the clinician or other user has advanced the intraluminal imaging probe 102 into the portion of the lumen 300 indicated by the instruction 670, the clinician or other user then activates or confirms the bookmark, e.g., by double-clicking on it, or by dragging and dropping it onto the current intraluminal image 510 in the intraluminal imaging display screen 500, or by issuing a vocal command to confirm the bookmark for the current intraluminal image 510. When this is done, the bookmark 680 is automatically associated not only with the current intraluminal image 510, but with the corresponding locations on the ILD 520 and graphical roadmap 530. In addition, the automatic and assisted bookmarking system automatically populates a label 550 that is automatically associated with the bookmark 680 and the current intraluminal image and may include, for example, the bookmark information, image location, and image type (e.g., reference, pre-treatment target, post-treatment target, etc.) In some embodiments, these steps are performed automatically by the automatic and assisted bookmarking system, without the need for user input of any kind, based on image recognition to track known bifurcations of a vessel or lumen as anatomic landmarks. Bookmarks may also be suggested or automatically placed based on automated image recognition of issues such as thrombus, webbing, and compression (venous) or stenosis (arterial).

Examples of border detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

Figure 7:
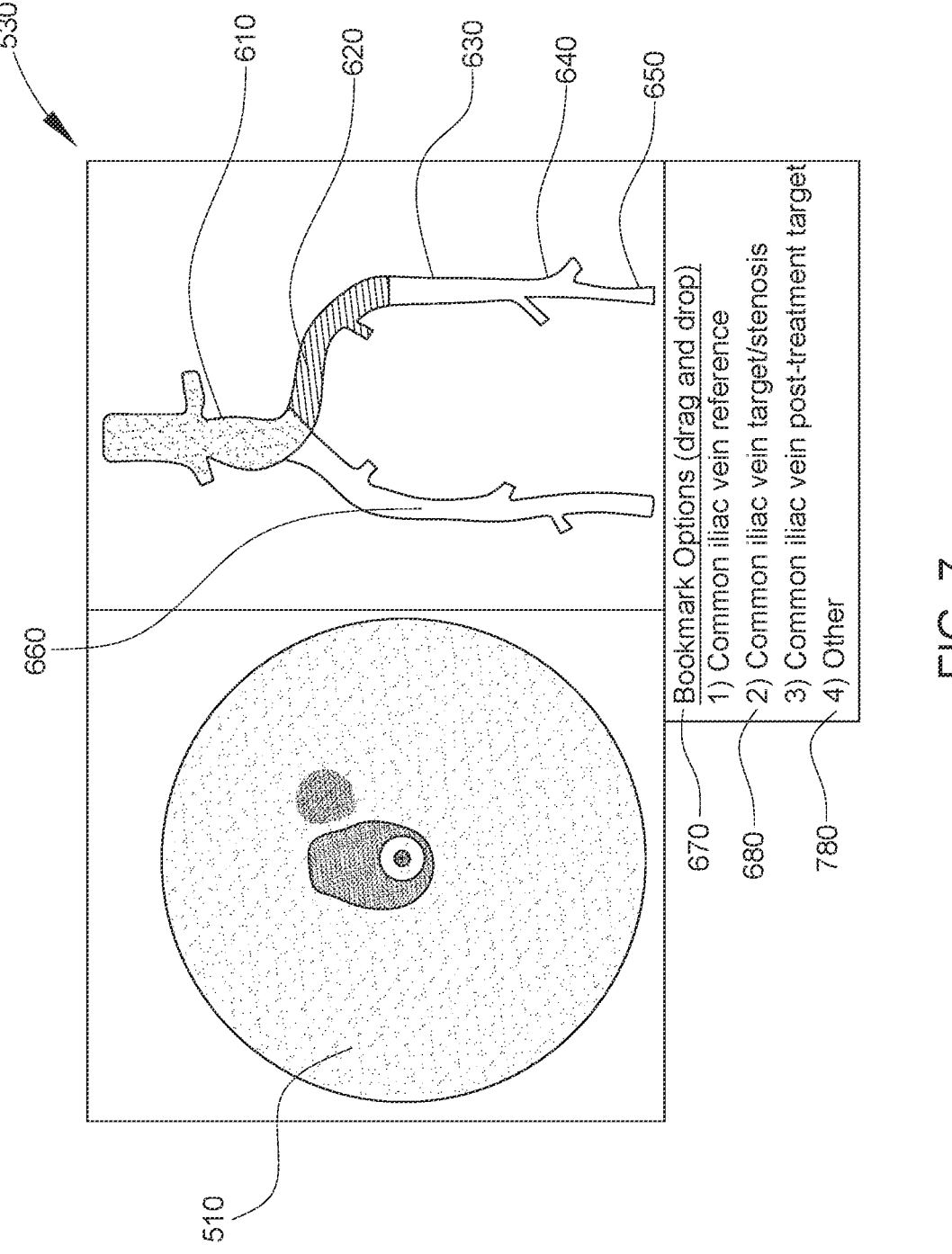
FIG. 7 shows a graphical roadmap screen display of an exemplary automatic and assisted bookmarking system during a pullback procedure in a left leg vein of a patient, in accordance with at least one embodiment of the present disclosure.

FIG. 7 shows a graphical roadmap screen display 530 of an exemplary automatic and assisted bookmarking system during a pullback procedure in a left leg vein of a patient, in accordance with at least one embodiment of the present disclosure. As with the example of FIG. 6, the graphical roadmap screen display includes multiple vein segments 610, 620, 630, 640, and 650. The corresponding segments on the right side 660 are also shown for reference, but are grayed out. In this example, the screen display also includes a tomographic image 510. In this example, rather than offering a single instruction 670 and suggesting a single bookmark 680, the automatic and assisted bookmarking system offers a menu 670 that includes multiple different suggested markers (e.g., bookmarks) 680 that are based the system's knowledge of the procedure being undertaken and direction of probe movement, along with an approximate but imperfect knowledge of the location of the intraluminal imaging probe 102 within the lumen 300. In this example, the system also offers an "Other" option 780 that permits the clinician or other user to enter marker information (e.g., bookmark and label information) manually. This may be useful for example during nonstandard procedures, or during procedures where the positioning information for the intraluminal probe 102 is believed to be inaccurate. Inputs from the user allow the system to select a desired bookmark from among the suggested bookmarks 680 and 780. In an example, the bookmark can be dragged and dropped onto either the tomographic image 510 or the roadmap image 530, and it will automatically be applied to both at the location corresponding to the currently displayed tomographic image.

In an example, a bookmark is a location marker on a pullback (e.g., on an ILD, roadmap, or cross-sectional tomographic image) that facilitates easy navigation. A label is a text annotation that can be associated with a region in a frame or a pullback, or even a bookmark. A bookmark can look like a little flag, or mark in a longitudinal view or roadmap. A label may comprise text that may or may not be associated with a bookmark.

Figure 8:
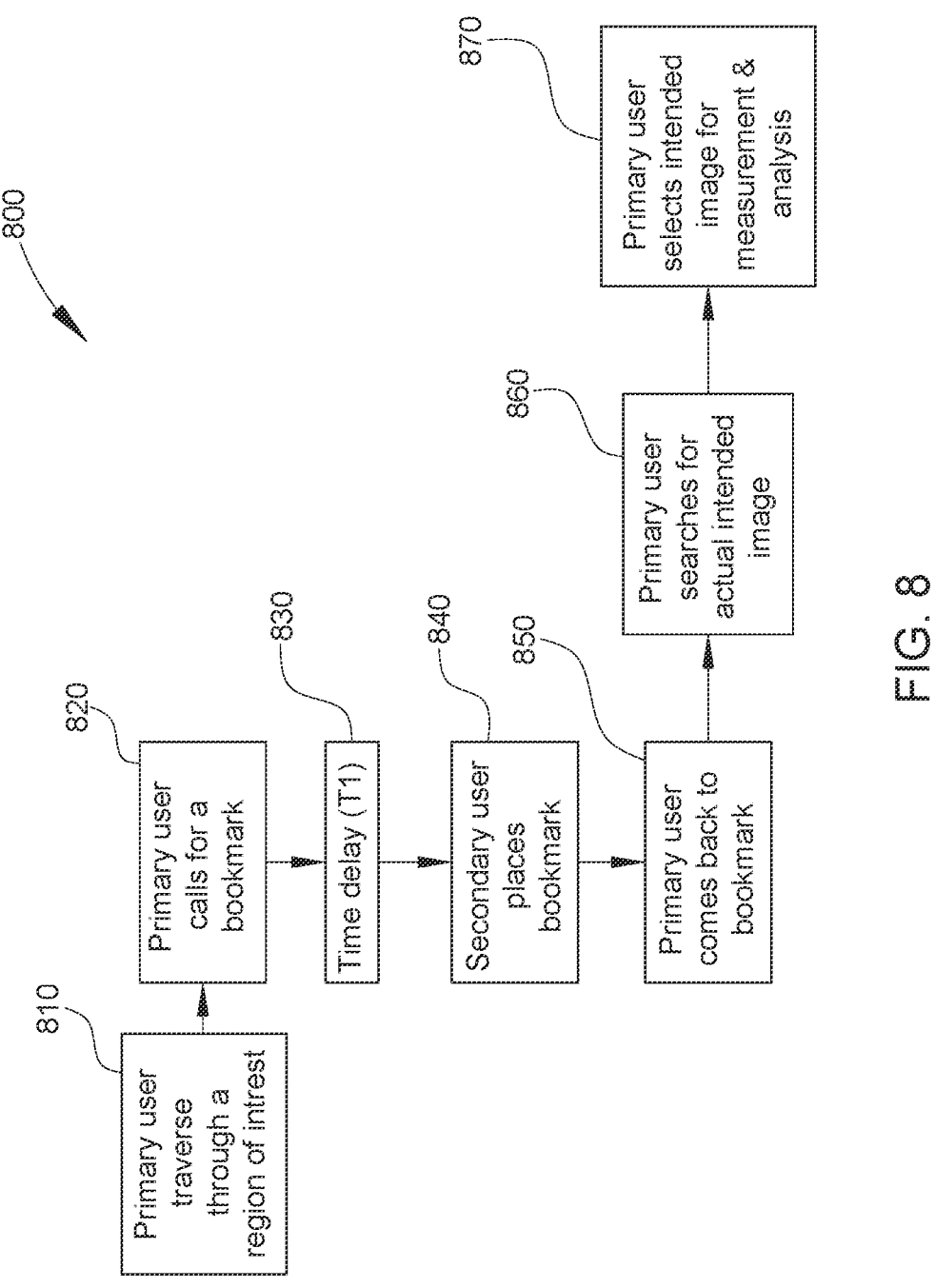
FIG. 8 is a flow diagram for an intraluminal image bookmarking method according to the related art.

FIG. 8 is a flow diagram 800 for an intraluminal image bookmarking method according to the related art. In step 810, a primary user (e.g., a clinician) pushes or pulls the intraluminal imaging probe 102 through a region of interest within the lumen 300. The region of interest may for example be a target region where diseased or compressed tissue is to be inspected, or a reference region where the dimensions of the lumen 300 may be recorded for comparison purposes.

In step 820, the primary user calls for a bookmark to label the current intraluminal imaging frame. However, in general the primary user does not stop moving the intraluminal imaging probe 102, but continues pushing or pulling it at a near-constant speed.

Step 830 represents an inevitable time delay between the primary user calling for a bookmark and a secondary user (e.g., a surgical assistant or non-sterile staff member) actually entering the bookmark information. This time delay is represented by the variable T1.

In step 840, the secondary user enters the bookmark information. This may involve typing in the current or suspected location of the intraluminal imaging probe 102, along with information about the type of image (e.g., target or reference). This data entry also takes time, represented by the variable T2. Meanwhile, in a typical intraluminal imaging procedure, the intraluminal imaging probe 102 continues moving at a relatively constant speed.

Once the imaging procedure (e.g., an IVUS pullback procedure) has been completed, in step 850 the primary user reviews the intraluminal imaging data in a review mode of the intraluminal imaging system 100, and locates the bookmark 540 that was placed by the secondary user. Very frequently, because of time delays T1 and T2, the bookmark has been placed on a later frame than the intended frame. In some instances, the bookmark may be placed on an earlier than intended frame if the secondary user has anticipated and attempted to compensate for the time delays T1 and T2.

In step 860, the primary user pages through the intraluminal images 510 and/or the ILD 520 to find the image 510 where the bookmark 540 was intended to be placed.

In step 870, the primary user relocates the bookmark 540 to the desired image 510, or deletes and re-enters the bookmark 540. The primary user then performs measurements, annotations, and other analysis of the bookmarked image 510.

This process is time consuming and error prone, creating a need in the art for improved tools and procedures.

Figure 9:
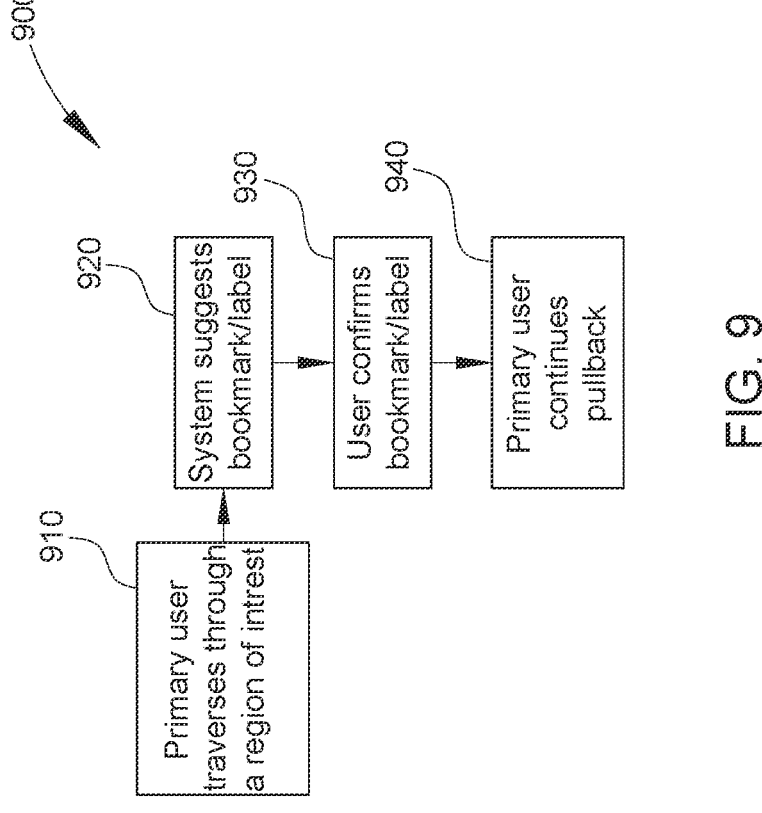
FIG. 9 is a flow diagram for an intraluminal image bookmarking method according to at least one embodiment of the present disclosure.

FIG. 9 is a is a flow diagram for an intraluminal image bookmarking method 900 according to at least one embodiment of the present disclosure. In step 910, the primary user (e.g., a clinician) pushes or pulls the intraluminal imaging probe 102 through a region of interest within the lumen 300. The region of interest may for example be a target region or a reference region.

In step 920 the automatic and assisted bookmarking method 900 suggests a bookmark 680 and/or associated label information 550 to the primary user. Based on the system's knowledge of the procedure type being performed, the point of entry, the direction of movement of the intraluminal imaging probe, and the location of the intraluminal imaging probe, the system is able to anticipate what bookmarks will be needed, and in what order. In an example, the user may for example specify jugular entry or femoral entry, and the direction of movement (e.g., pullback or forward longitudinal movement). A typical procedure might for example involve pullback from either the abdomen to the leg or from the leg to the abdomen. The system knows the order and reverse order in which vessel segments occur (EIV, CIV, etc.) and presents them in the correct order based on the entry point and direction of movement.

In step 930, a user (either the primary user or a secondary user) confirms the bookmark and/or associated label information. This confirmation may be performed for example by dragging and dropping the bookmark 680 onto the current intraluminal image 510, or by double-clicking on the bookmark 680, or by issuing a spoken confirmation to a voice recognition interface of the automatic and assisted bookmarking system (e.g., the processor circuit is receiving an electrical signal representative of the spoken confirmation). Thus, the bookmark 680 is placed directly onto the desired frame during the pullback procedure, and requires no rework during a review stage.

In step 940, the primary user continues moving the intraluminal imaging probe 102 at a constant speed through the lumen. In some instances, the system may return to step 920 and suggest additional bookmarks during the procedure. In other instances, the process is complete after step 940.

Another aspect of the automatic and assisted bookmarking system is to present the user with multiple neighboring frames around the bookmarked frame. In the workflow illustrated in FIG. 8, the primary user doesn't usually get the bookmark placed at the right frame because of the time delay associated with T1 and perhaps T2. Some embodiments of the present disclosure assist the user by recording a set of frames or a short video clip around the bookmark that allows the user to have more confidence that the frame of interest is actually captured by the bookmark. The user can then select the actual frame during case review without accessing the main pullback itself for reporting or studying in the current case. Further, if the bookmark is edited in any of these frames, the change will be applied to all of them (and may also be applied to ILD or roadmap images), thus simplifying the bookmark editing workflow.

Figure 10:
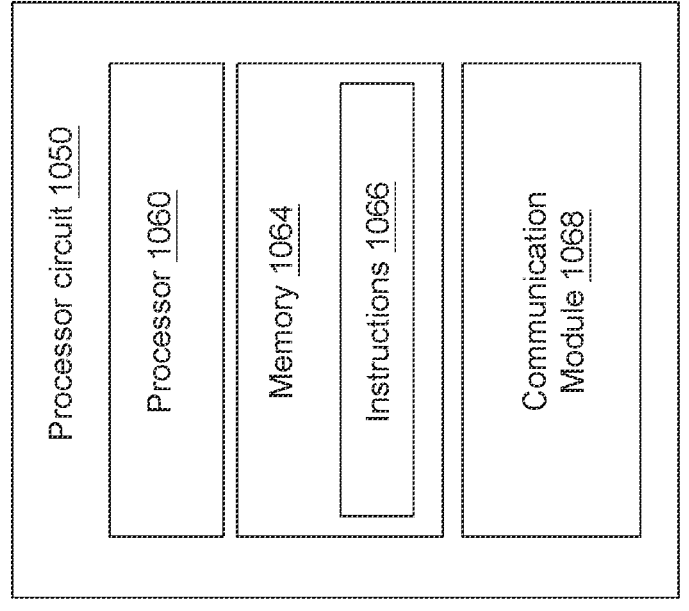
FIG. 10 is a schematic diagram of a processor circuit, according to embodiments of the present disclosure.

FIG. 10 is a schematic diagram of a processor circuit 1050, according to embodiments of the present disclosure. The processor circuit 1050 may be implemented in the ultrasound imaging system 100, or other devices or workstations (e.g., third-party workstations, network routers, etc.), or on a cloud processor or other remote processing unit, as necessary to implement the method. As shown, the processor circuit 1050 may include a processor 1060, a memory 1064, and a communication module 1068. These elements may be in direct or indirect communication with each other, for example via one or more buses.

The processor 1060 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1060 may also comprise another hardware device, a firmware device, or any combination thereof configured to perform the operations described herein. The processor 1060 may also be implemented as a combination of computing devices, e.g., a combination of a DSP and a microprocessor, a plurality of microprocessors, one or more microprocessors in conjunction with a DSP core, or any other such configuration.

The memory 1064 may include a cache memory (e.g., a cache memory of the processor 1060), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1064 includes a non-transitory computer-readable medium. The memory 1064 may store instructions 1066. The instructions 1066 may include instructions that, when executed by the processor 1060, cause the processor 1060 to perform the operations described herein. Instructions 1066 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 1068 can include any electronic circuitry and/or logic circuitry to facilitate direct or indirect communication of data between the processor circuit 1050, and other processors or devices. In that regard, the communication module 1068 can be an input/output (I/O) device. In some instances, the communication module 1068 facilitates direct or indirect communication between various elements of the processor circuit 1050 and/or the ultrasound imaging system 100. The communication module 1068 may communicate within the processor circuit 1050 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

Figure 11:
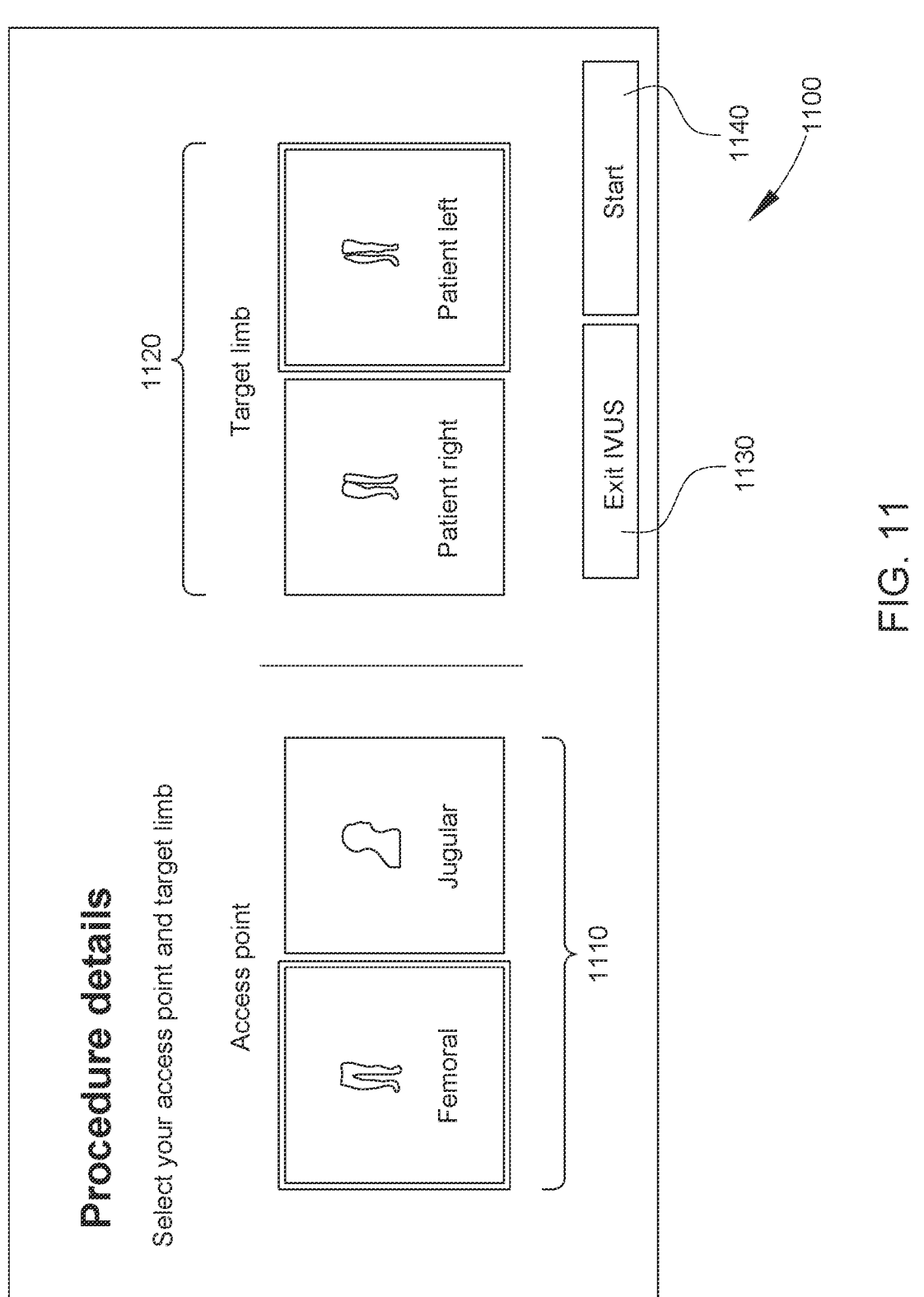
FIG. 11 is a screenshot of an IVUS access point selection screen, in accordance with at least one embodiment of the present disclosure.

FIG. 11 is a screenshot of an IVUS access point selection screen 1100, in accordance with at least one embodiment of the present disclosure. The automatic and assisted bookmarking system may be generally capable of automatically identifying different regions of a patient's circulatory system by using a machine-learning algorithm or other training-based AI algorithm to match IVUS images against an a priori dataset or knowledge set of statistically representative lumen anatomy for different human subpopulations. However, the accuracy of vessel identification is improved when the IVUS pullback venogram system begins with accurate and specific information about the starting point and direction of travel of the ultrasound transducer 124 of the imaging catheter 102. In this example, the screen display 1100 therefore includes an access point selector 1110 that permits a clinician or other user to select between femoral access and jugular access. The screen display 1100 also includes a target limb selector 1120 that permits a clinician or other user to select between a patient's right leg and left leg as the location of the IVUS pullback. These examples are merely illustrative; other access points and target limbs, target regions (e.g., the abdomen), or target anatomy (e.g., the heart) are also possible and may be used instead or in addition, depending on the procedure type, disease type, and location of the anatomical features of interest.

Also visible are an exit button 1130 and a start button 1140. Other controls may also be provided including but not limited to help buttons, procedure type selectors, disease type selectors, and anatomy type selectors.

A number of variations are possible on the examples and embodiments described above. For example, the automatic and assisted bookmarking system may be employed in anatomical systems within the body other than those described, or may be employed to image other disease types, object types, or procedure types than those described. The technology described herein may be applied to intraluminal imaging sensors of diverse types, whether currently in existence or hereinafter developed. The system may be employed with IVUS for coronary arterial and peripheral use in arterial or venous imaging, such as Philips' IGT-D devices and IVUS console software. Alternatively or in addition, the system may be employed with X-ray, angiogram, and venogram applications that require or enable labels and bookmarks. The system may be employed with any imaging modality that employs labels or bookmarks, but with allowed editing of those findings.

Accordingly, the logical operations making up the embodiments of the technology described herein are referred to variously as operations, steps, objects, elements, components, or modules. Furthermore, it should be understood that these may occur or be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the automatic and assisted bookmarking system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the automatic and assisted bookmarking system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An apparatus, comprising:
an intravascular imaging catheter; and
a processor circuit configured for communication with the intravascular imaging catheter, wherein the processor circuit is configured to:
   receive a plurality of intravascular images obtained by the intravascular imaging catheter during movement of the intravascular imaging catheter within vasculature comprising a plurality of blood vessels that are continuous with one another;
   output, to a display in communication with the processor circuit, a screen display comprising:
      a first graphical representation of the vasculature, wherein the first graphical representation comprises a combined longitudinal cross-sectional view of the plurality of blood vessels such that different portions of the combined longitudinal cross-sectional view are representative of the plurality of blood vessels;
      a plurality of target markers distributed longitudinally along the combined longitudinal cross-sectional view; and
      a plurality of reference markers distributed longitudinally along the combined longitudinal cross-sectional view,
   wherein each of the plurality of target markers and each of the plurality of reference markers corresponds to a respective intravascular image of the plurality of intravascular images,
   wherein each of the different portions comprises a target marker and a reference marker such that the target marker and the reference marker are provided on the combined longitudinal cross-sectional view for each blood vessel of the plurality of blood vessels,
   wherein each target marker is representative of a target location of a respective blood vessel, and
   wherein each reference marker is representative of a reference location of the respective blood vessel,
   wherein, for the respective blood vessel, a diameter or a cross-sectional area of the reference location is larger than a diameter or a cross-sectional area of the target,
   wherein at least one of the plurality of target markers is representative of a compression or a blockage, and
   wherein at least one of the plurality of reference markers is representative of a healthy tissue.

2. The apparatus of claim 1, wherein the vasculature comprises a peripheral vasculature.

3. The apparatus of claim 2, wherein the vasculature comprises a peripheral venous vasculature.

4. The apparatus of claim 3, wherein the plurality of blood vessels comprises two or more of: a common iliac vein (CIV), an external iliac vein (EIV), or a common femoral vein (CFV).

5. The apparatus of claim 1, wherein the plurality of blood vessels comprises a first blood vessel and a second blood vessel such that:
   the plurality of target markers comprises a first target marker for the first blood vessel and a second target marker for the second blood vessel; and
   the plurality of reference markers comprises a first reference marker for the first blood vessel and a second reference marker for the second blood vessel.

6. The apparatus of claim 1,
wherein the screen display comprises a plurality of numerals configured to indicate a plurality of values associated with an anatomical feature along the vasculature,
wherein the plurality of numerals is distributed longitudinally along the combined longitudinal cross-sectional view,
wherein each numeral is positioned proximate to a corresponding portion of the combined longitudinal cross-sectional view representative of the respective blood vessel.

7. The apparatus of claim 1,
wherein the screen display further comprises a second graphical representation of the vasculature different than the longitudinal cross-sectional view,
wherein the plurality of target markers and the plurality of reference markers are overlaid on the second graphical representation.

8. The apparatus of claim 7,
wherein the second graphical representation comprises a stylized diagram of the plurality of blood vessels,
wherein the stylized diagram depicts a curvature of the vasculature.

9. The apparatus of claim 1, wherein the intravascular imaging catheter comprises an intravascular ultrasound (IVUS) imaging catheter.

10. The apparatus of claim 1, wherein the intravascular imaging catheter comprises an optical coherence tomography (OCT) imaging catheter.

11. The apparatus of claim 1,
wherein a quantity of the plurality of target markers matches a quantity of the plurality of blood vessels and a quantity of the different portions of the longitudinal cross-sectional view, and
wherein a quantity of the plurality of reference markers matches the quantity of the plurality of blood vessels and the quantity of the different portions of the longitudinal cross-sectional view.

12. The apparatus of claim 1, wherein the longitudinal cross-sectional view of the blood vessel comprises a stack of the plurality of intravascular images.

13. The apparatus of claim 1, wherein the combined longitudinal cross-sectional view comprises a straight orientation in the screen display.

14. The apparatus of claim 1,
wherein the screen display comprises a plurality of text labels configured to indicate that the different portions of the combined longitudinal cross-sectional view are representative of the plurality of blood vessels,
wherein the plurality of text labels is distributed longitudinally along the combined longitudinal cross-sectional view,
wherein each text label is positioned proximate to a corresponding portion of the combined longitudinal cross-sectional view representative of the respective blood vessel.

15. The apparatus of claim 3, wherein the plurality of blood vessels comprises a common iliac vein (CIV), an external iliac vein (EIV), and a common femoral vein (CFV), wherein the different portions of the combined longitudinal cross-sectional view comprise:

a CIV portion comprising a CIV target marker and a CIV reference marker;

an EIV portion comprising an EIV target marker and an EIV reference marker; and a CFV portion comprising a CFV target marker and a CFV reference marker.

16. The apparatus of claim 5, wherein the different portions of the combined longitudinal cross-sectional view comprise a first portion representative of the first blood vessel and a second portion representative of the second blood vessel, wherein the first portion comprises the first target marker and the first reference marker, wherein the second portion comprises the second target marker and the second reference marker, wherein the first target marker, the first reference marker, the second target marker, and the second reference marker are positioned proximate to one another along the combined longitudinal cross-sectional view.

\* \* \* \* \*